United States Patent [19]   [11] 4,018,837
Archer et al.   [45] Apr. 19, 1977

[54] STABILIZED METHYLCHLOROFORM

[75] Inventors: Wesley L. Archer, Midland; Elbert L. Simpson, Auburn; Raymond R. Gerard, Bay City, all of Mich.

[73] Assignee: The Dow Chemical Company, Midland, Mich.

[22] Filed: Nov. 25, 1974

[21] Appl. No.: 527,003

Related U.S. Application Data

[63] Continuation-in-part of Ser. No. 281,242, Aug. 16, 1972, abandoned, and a continuation-in-part of Ser. No. 281,243, Aug. 16, 1972, abandoned, and a continuation-in-part of Ser. No. 281,244, Aug. 16, 1972, abandoned, and a continuation-in-part of Ser. No. 281,245, Aug. 16, 1972, abandoned.

[52] U.S. Cl. ..................................... 260/652.5 R
[51] Int. Cl.$^2$ ..................................... C07C 17/42
[58] Field of Search ............ 260/652.5 R; 281/242, 281/245, 243, 244

[56] References Cited

UNITED STATES PATENTS 3,723,331  3/1973  Correia .................. 260/652.5 R

*Primary Examiner*—D. Horwitz
*Attorney, Agent, or Firm*—Glwynn R. Baker

[57] ABSTRACT

A stable 1,1,1-trichloroethane composition containing 1,1,1-trichloroethane and, as the essential acid acceptor, 0.25 to 1 weight percent of a $C_{4-8}$ monoepoxide, epichlorohydrin or a mixture of such epoxides and, as the essential stabilizer against metal-induced decomposition, 3.5 to 4.5 weight percent of a three-component system selected from the group consisting of:
  dioxane,
  trioxane,
  dioxolane,
  t. butyl alcohol, and
  a $C_{1-3}$ nitroalkane or mixtures of nitroalkanes, in a proportion one to the other within the shaded areas of FIGS. 1–9, provided that when a nitroalkane is not present as a member of the three-component mixture, it is added in an amount to provide from about 0.25 to 1 percent by weight of said nitromethane.

The composition set forth balances inhibitor content to obtain protection in both the liquid and vapor without excessive losses or concentrations disproportionate with solvent losses through vapor escape or liquid drag-out.

Thus the above compositions are stable in the presence of the metals aluminum, zinc, iron, copper and their alloys, both in the liquid and vapor state of the compositions. The compositions do not partition in a manner to concentrate the low boiling stabilizers in the vapor or the high boiling stabilizers in the liquid even after refluxing over extended periods of time accompanied by frequent additions of make-up volumes of stabilized 1,1,1-trichloroethane to compensate for the solvent losses.

11 Claims, 9 Drawing Figures

STABILIZED METHYLCHLOROFORM

CROSS REFERENCE TO RELATED APPLICATIONS

This application is a continuation-in-part of our co-pending applications, Ser. Nos. 281,242, 281,243, 281,244 and 281,245, each filed on Aug. 16. 1972, each now abandoned.

BACKGROUND OF THE INVENTION 1,1,1-trichloroethane (methylchloroform) has become a promising solvent for the metal working and textile industries because of its low toxicity and good ecological properties and is being widely used by industry to replace both trichloroethylene and perchloroethylene. However, 1,1,1-trichloroethane is known to exhibit a high degree of instability in the presence of aluminum, and/or iron and/or copper and/or their alloys and when certain inhibitors are present to increase stability, then often zinc becomes a problem.

The art in some ninety odd U.S. patents alone discloses literally hundreds of compounds as exhibiting some inhibiting effect on 1,1,1-trichloroethane in the presence of metals and acids, principally the inorganic acid hydrogen chloride. The early stabilizers such as tertiary butyl alcohol which prevented rapid deterioration of 1,1,1-trichloroethane in the cold but was substantially ineffective when the solvent was used hot, and secondary butyl alcohol which was employed as a storage stabilizer to prevent discoloration from contact during storage in iron drums, gave way quickly to 1,4-dioxane alone and in combination with non-primary alcohols which rapidly broadened the areas of use into which this solvent could be safely employed. This stabilizer system was disclosed in U.S. Pat. No. 2,811,252. Shorly after introduction of 1,4-dioxane it was disclosed in U.S. Pat. No. 2,923,747 that nitromethane could contribute to the stabilization when used in combination with 1,4-dioxane. Ultimately, epoxides were found (U.S. Pat. No. 3,049,571) to enhance even the 1,4-dioxane and nitromethane as well as the non-primary alcohols. The advent of this latter discovery opened the way to cautious usage of 1,1,1-trichloroethane in vapor degreasing. Other commercial compositions began to find their way into the marketplace until today some five additional 1,1,1-trichloroethane compositions are on the market.

These compositions contain (a) 1,3-dioxolane, nitromethane, butylene oxide, isobutyl alcohol and toluene; (b) butylene oxide, acetonitrile, trioxane and nitromethane; (c) tertiary butyl alcohol, nitromethane and methyl butynol; (d) butylene oxide, tertiary amyl alcohol, methyl ethyl ketone, and nitromethane; and, (e) nitromethane, acetonitrile, butylene oxide and isopropyl nitrate. Thus, commercially only a few of the literally hundreds of compounds disclosed in the patent literature are useful under the stringent industrial conditions.

To establish the state of the art at the time this invention was made, a Table is hereafter set forth detailing in tabular form the patent literature most closely related to the present invention.

| Component | 2,811,252 | 2,933,747 | 3,049,571 | 3,000,978 | 3,070,634 | 3,099,694 | 3,113,156 | 3,265,747 | 3,238,137 |
|---|---|---|---|---|---|---|---|---|---|
| Methyl ethyl ketone | | | | | | | | | |
| Trimethylorthoformate | | | | | | | | | |
| Alkyl cyanide | | | | | | | | | |
| Monoolefin | | | | | | | | | |
| Toluene | | | | | | x | | | |
| Nitriles | | | | | | | | | |
| Furans | | | | | | | | | |
| Ethyl acetate | | | | | | | | | |
| Oxazole | | | | | | | | | |
| Amines | | | | | | | | | |
| 1,2-dimethoxy ethane | | x | | | | | x | | |
| Perchloroethylene | | | | | | | | | |
| Nitroalkanes (nitromethane) | | | | | | | | | |
| Dioxadiene | | | | | | | | | |
| Dioxene | | | | | | | x | | |
| Trioxane | | | | | | x | | | |
| Dioxolane | | | | | | x | | x | x |
| Dioxane | x | x | x | | x | | | x | |
| Butylene oxide/oxiranes | o | | x | x | X* | | | | |
| Acetylenic alcohols | o | | | | /X | | | /X | |
| Secondary alcohols | o | | | | /X | | | /X | |
| Tertiary alcohols | /X | | | | /X | | | /X | |
| Primary alcohols | /X | | | | | | | | |
| N-methyl pyrrole | /X | | | | | | | | |

| Component | 3,251,891 | 3,326,988 | 3,326,989 | 3,360,575 | 3,397,148 | 3,445,523 | 3,505,415 | 3,532,761 | 3,549,715 | 3,564,061 | 3,665,747 | 3,676,355 |
|---|---|---|---|---|---|---|---|---|---|---|---|---|
| Methyl ethyl ketone | | | | | | | Alkoxy Group + any of list | /X | | | | |
| Trimethylorthoformate | | | | | | | | | | | | |
| Alkyl cyanide | | | | | | | | | | | | |
| Monoolefin | | | | | | | | | | | | |
| Toluene | | | | | x | | | | | | | |
| Nitriles | x | | | | | x | | /X | | | | /X |
| Furans | | | x | | | | | | | | | |
| Ethyl acetate | | | | | | | | | | | | |
| Oxazole | | | | | | | | | | | | x |
| Amines | | | | /X | | | | | | | | |
| 1,2-dimethoxy ethane | | | x | | | | | | | | | |
| Perchloroethylene | | | | | | | | | | | | |
| Nitroalkanes (nitromethane) | x | x | x | /X | | | | | /X | | | |
| Dioxadiene | | | | | | | | | | /X | | |
| Dioxene | | | | /X | | | | | | | | |
| Trioxane | | | | /X | | | | | | | | |
| Dioxolane | x | | | /X | x | | | | | | | |
| Dioxane | | | | | x | | | | | | | |
| Butylene oxide/oxiranes | /X | /X | x | /X | | /X | | /X | /X | /X | /X | /X |
| Acetylenic alcohols | /X | /X | | /X | | /X | | /X | /X | /X | X | /X |
| Secondary alcohols | /X | /X | | /X | | /X | | X | /X | /X | | /X |
| Tertiary alcohols | /X | /X | x | /X | | /X | | | /X | | X | /X |
| Primary alcohols | /X | /X | | /X | | /X | | Oxetane | | /X | | /X |
| N-methyl pyrrole | | | | | | | | | | x | | |

*A slash line (/) before an X means the component is optional or merely suggested as a possible additional component.

It is apparent from the above Table that while many of the compounds and mixtures of compounds are capable of preventing the aluminum reaction in the laboratory tests, they are not widely used in commercial applications because of cost, availability, toxicity, loss through evaporation when the compositions are heated in use, etc. It is with such lists of compounds and their shortcomings in mind that the present invention was made.

The criteria for establishing a commercial grade of 1,1,1-trichloroethane which has unrestricted utility in industry should include an equal degree of stability of the liquid and its vapors, less than about ten (10%) percent total inhibitors and a substantial ability to be distilled without loss of stability by concentration of the low boilers in the overhead and their subsequent loss from the system and high boilers in the bottoms of the still through improper or inefficient still operation, and the like. Even today these criteria are not all found in the commercial compositions.

The compounds which are combined in accordance with the present invention have been disclosed in the art and in some instances have been used commercially. However, each lacks one or more properties which requires its combination with one or more compounds which also lack some other property required; thus, the necessity to balance a stabilizer composition. To demonstrate this phenomenon, the compounds combined in accordance with the present invention are each set forth with the property or properties they lack as stabilizer components.

|  | DIOXANE | DIOXOLANE | TRIOXANE | 1<br>$CH_3NO_2$ | 2<br>TBA | 3<br>BO |
|---|---|---|---|---|---|---|
| High boiling build-up in sump | — |  | — |  |  |  |
| Excessive loss to vapors |  |  |  | — | — | — |
| Zinc attack | — | — | — |  | — |  |
| Inadequate protection in presence of Al-copper containing alloy (2024 Al) in both phases | — | — | — |  | — |  |
| Loss in presence of iron and water |  |  |  | — |  |  |
| Loss to vapor build-up in sump | — |  | — |  | — | — |
| Order of activity to 1100 Al | 1 | 4 | 2 | 3 | 5 | 6 |

1 - Nitromethane
2 - t. butyl alcohol
3 - Butylene oxide

To demonstrate the significance of order of activity with respect to 1100 aluminum the equivalency of each compound, i.e., the least amount of the compound required to prevent attack on 1100 aluminum in either phase is set forth:

| wt. % | 1.6* | 2.6 | 3.1 |
|---|---|---|---|
|  | dioxane ≅ | trioxane ≅ | nitromethane ≅ |
|  | 4.0 | 4.2 | 9.8 |
|  | dioxolane ≅ | t. butyl alcohol ≅ | butylene oxide |

*(Waring Blendor test APHA color index <1000).

If further these compounds are compared as to the minimum amount required in an initial charge of solvent to stabilize both top and bottom after partitioning (50% by volume overhead), the following is obtained:

| wt. % | 3.4 | 4.4 | 4.4 |
|---|---|---|---|
|  | dioxane ≅ | nitromethane ≅ | dioxolane ≅ |
|  | 5.0 | 8.2 | 12.2 |
|  | trioxane ≅ | t. butyl alcohol ≅ | butylene oxide |

Thus, it becomes apparent a major balancing is required but even this data with the prior art disclosures fails to teach or suggest what balance is required with what compounds. It is therefore an object of this invention to provide compositions which are effective at concentrations of from between about four (4%) percent to about six (6%) percent and which meet the criteria set out above.

BRIEF DESCRIPTION OF THE INVENTION

In accordance with the present invention, it has now been found that 1,1,1-trichloroethane can be stabilized in the liquid and vapor against deterioration in the presence of metals such as aluminum, zinc, copper and/or iron and/or their alloys and attack upon the metals by the decomposition products of the solvent or complexes of the metal decomposition products and/or solvent. The high degree of stabilization is obtained by incorporating a mixture of compounds from a select group in a total concentration in percentage by weight, of about 4.0 to about 6; to wit:

0.25–1 percent by weight of a monoepoxide, monochloroepoxide or mixture thereof having 3 to 8 carbon atoms as the essential acid acceptor;

3.5–4.5 weight percent of three components, selected from dioxane, dioxolane, trioxane, t. butyl alcohol and a $C_{1-3}$ nitroalkane or mixture of $C_{1-3}$ nitroalkanes each present in the percentages within the shaded areas of FIGS. 1–9 of the drawings and when nitromethane is not a component then about 0.25 to about 1% nitromethane is present.

FIGS. 1–9 represent graphic illustrations of compositions of the named three-component systems which when employed in accordance with the present invention, i.e., in combination with an epoxide and nitromethane, if the latter is not present in the three-component system, provide the protection of the solvent, both liquid and vapor, and metal in contact with the solvent, both liquid and vapor. The vertical line shaded area in each figure represents the compositions of the named ingredients which are effective at 3.5 weight percent of a mixture of the three ingredients in the proportions derivable from the graph. The 45° left-angled lined shaded area and the vertical lined area together represent the compositions of the named ingredients which are effective at 4.0 percent of a mixture of the three ingredients in the proportions derivable from the graph which fall within the scope of the present invention. The 45° right-angled lined shaded area plus the left-angled lined shaded area plus the vertical lined shaded area represent the compositions of the named ingredients which are effective at about 4.5 weight percent of a mixture of the three ingredients in the proportions derivable from the graph. The compositions within the shaded areas and which contain the additional stabilizer noted above, an epoxide and/or nitromethane if it is not present in the three-component mixture, are stable in their liquid form as well as their vaporous form, can be distilled with the distillate being stable to attack on and by metals, can be repeatedly vaporized and condensed, as in vapor degreasing, without loss of stability, and can be partially lost, as in vapor degreasing, with frequent make-up added without build-up of high boilers in the liquid.

While some of the formulations are shown to be operative outside the heavy line of the figure, it is not advisable to operate within this range since, for example, a composition along the binary line 1,4-dioxane-1,3-dioxolane will be stable in the liquid and vapor, the build-up of dioxane in the sump will be great enough that in several weeks as much as 10 to 20% dioxane can on occasion accumulate in the liquid posing a potential fire hazard and if the equipment has any zinc components, as many do, the attack on zinc will be very severe.

The epoxides which have been found useful are propylene oxide, butylene oxide, isobutylene oxide, the pentylene oxides, the hexylene oxides including cyclohexene oxide, heptylene oxides, the octylene oxides and epichlorohydrin. The preferred epoxides are propylene oxide, epichlorohydrin, butylene oxide, isobutylene oxide and mixtures of these oxides.

DETAILED DESCRIPTION OF THE INVENTION

Figure 1:
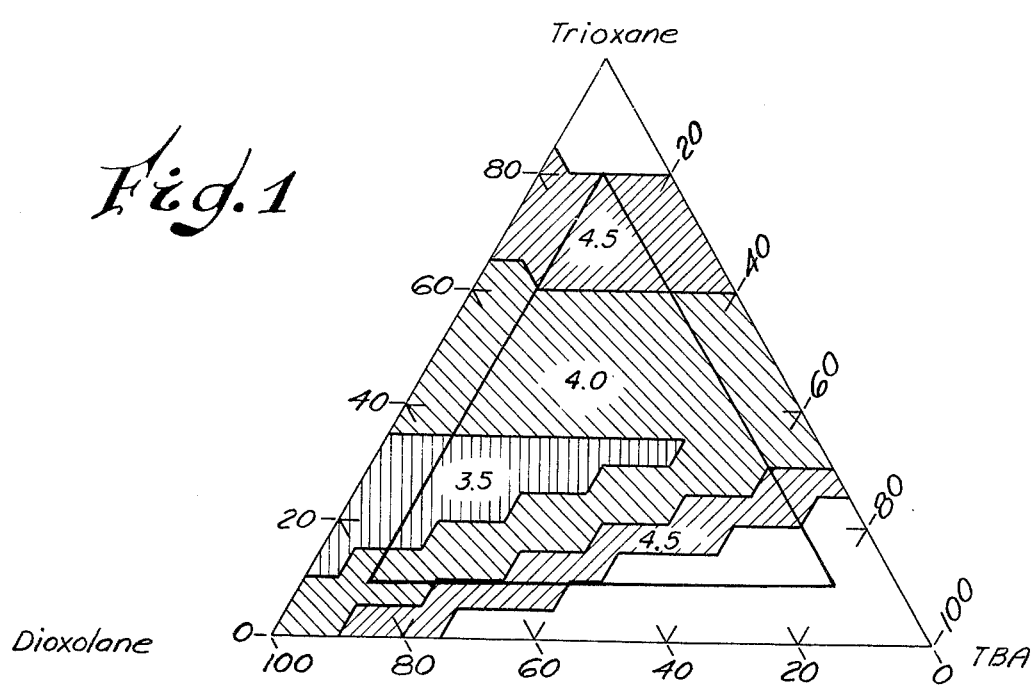
Figure 2:
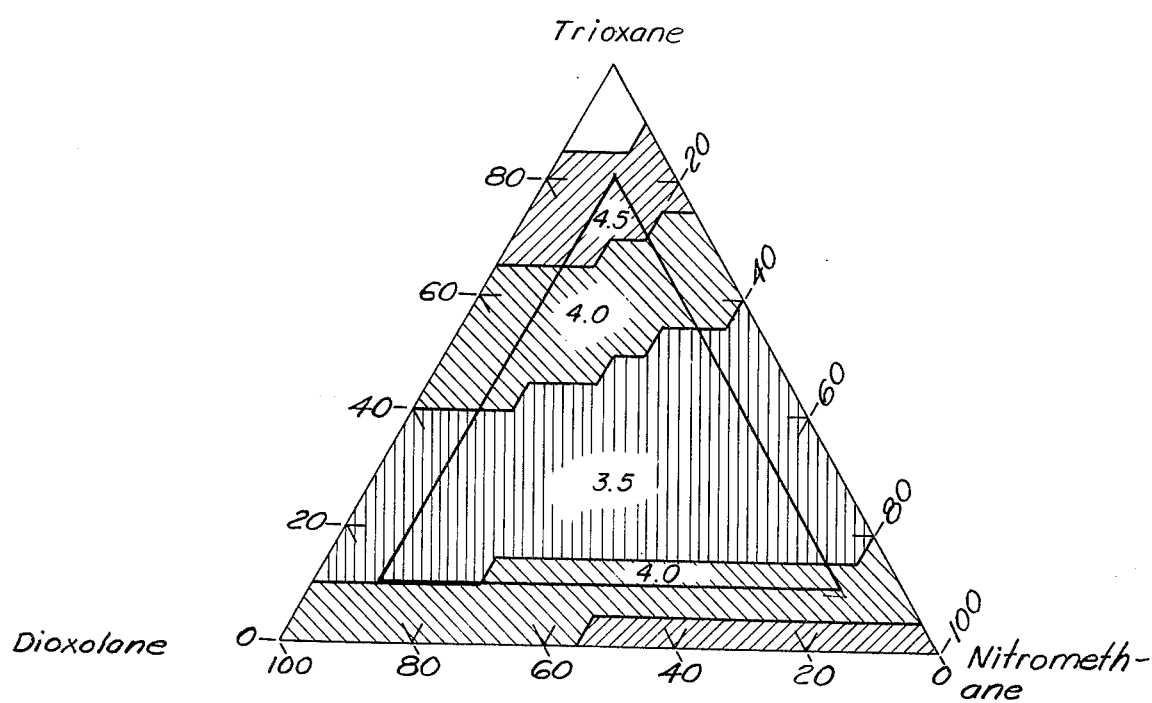
Figure 3:
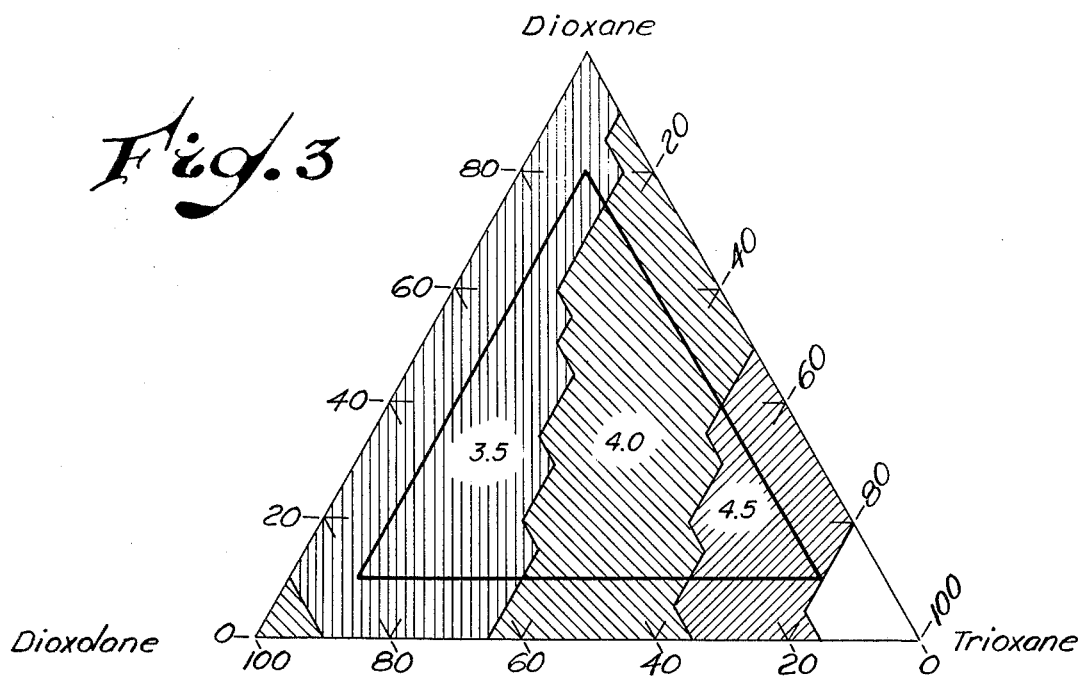
Figure 4:
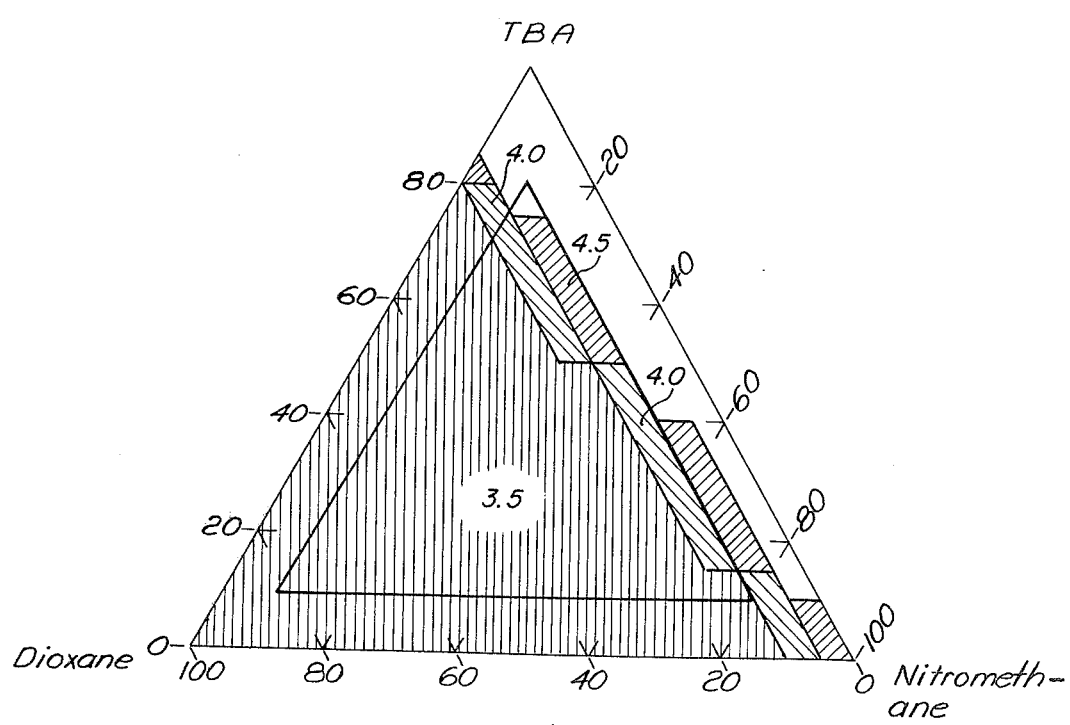
Figure 5:
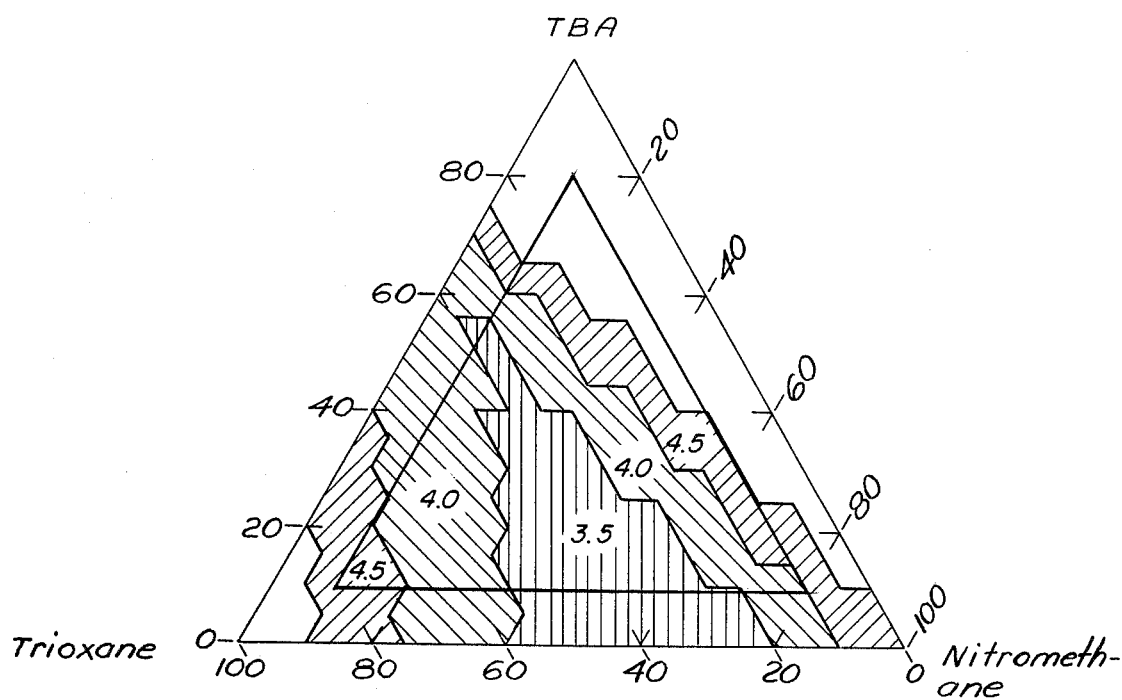
Figure 6:
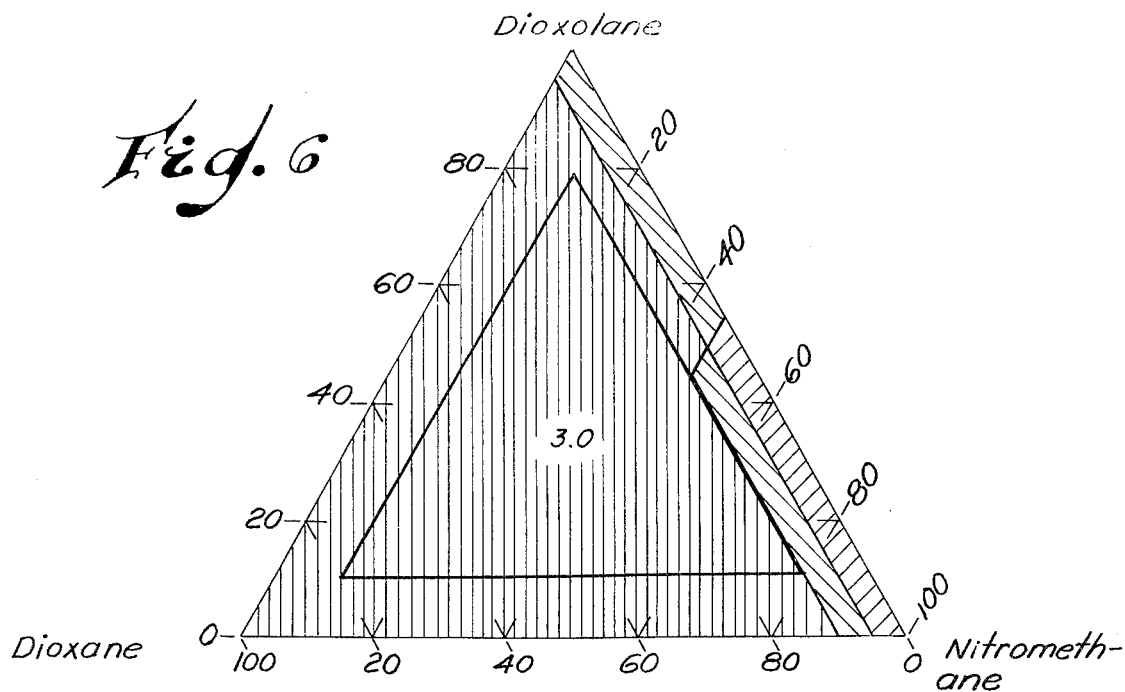
Figure 7:
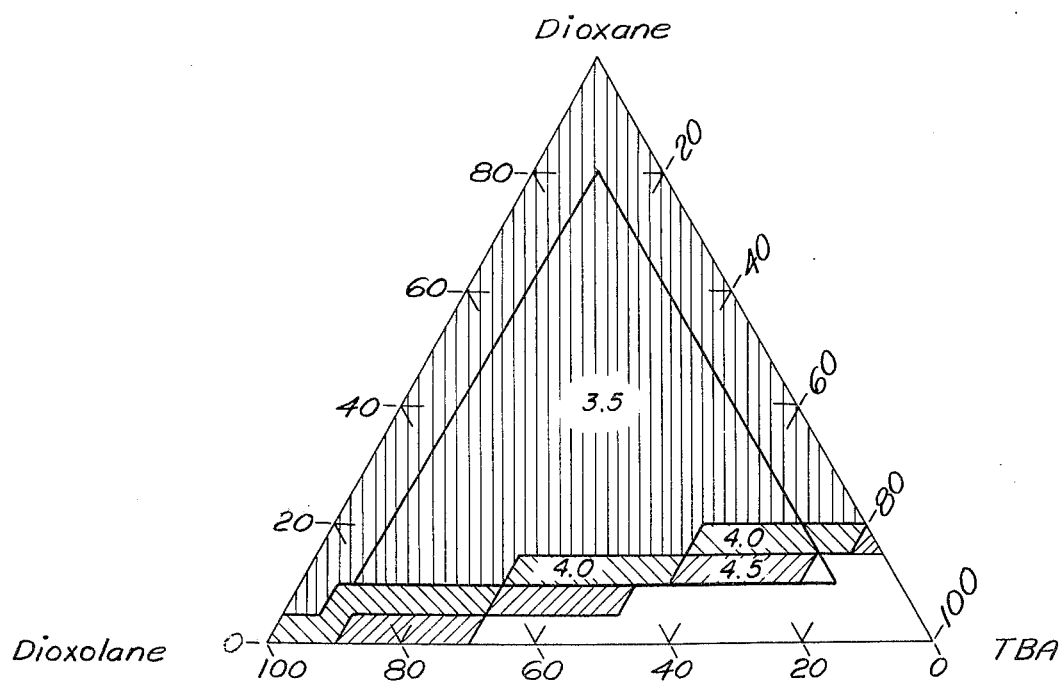

It has now been found that 1,1,1-trichloroethane containing from 3.5 to about 4.5 percent by weight of one of the compositions within the shaded areas as shown in FIGS. 1–9 of the drawings in combination with about 0.25 to about 1 percent by weight of a $C_{3-8}$ monoepoxide or chloromonoepoxide and nitromethane, if the latter is not present in the three-component systems, will be stable against deterioration in the presence of metals, particularly aluminum, zinc, copper and/or iron and/or their alloys in the liquid state and/or vapor state under the use conditions encountered in industry. Thus, compositions of 1,1,1-trichloroethane containing one of the compositions illustrated in the figures of the drawings and a nitroalkane and epoxide will remain substantially colorless, without deterioration or attack upon aluminum whether in the liquid or vapor state longer than known stabilized compositions. Tests employing the most effective known inhibitors illustrate that those which are illustrated in the figures of the drawings will satisfactorily stabilize 1,1,1-trichloroethane in the vapor and liquid state without, through partitioning, loss of inhibitors or build-up of inhibitors to a degree to affect stability and/or safety, will permit distillation without loss of inhibitors to below the safe level and will tolerate the presence of the common acidic contaminants, grease, oil and metal fines without losing their inhibiting qualities. All compositions must have at least 0.25 percent by weight of a $C_{3-8}$ monoepoxide or chloromonoepoxide, or mixture of two epoxides, and at least 3.5 percent by weight of a three-component mixture which, if nitromethane is not included, must be added in an amount of at least 0.25 weight percent.

EXAMPLES

A series of tests was conducted to determine the partitioning properties of the several compounds here employed. The partitioning experiment correlates with industrial practice by simulating the losses to the vapor of the solvent and its low boiling inhibitors and conversely the build-up in the sump of the high boiling inhibitors between additions of solvent to, for example, a vapor degreaser. Such a test procedure enables the laboratory to determine the build-up and losses through excessive losses of solvent in short periods as well as build-up over long periods of efficient operation. The apparatus consisted of a one liter round bottom flask with a standard taper joint. To this flask was attached a one liter round bottom flask which had been altered by placing a glass pipe through the bottom extending to a point in the interior such that the flask would hold 450 ml. of liquid to the upper lip of the pipe. The exterior portion of the pipe extending from the bottom was fitted into the neck of the first flask. A water condenser was fitted to the neck of the modified flask in a manner such that condensate dripping from its interior wall will fall into the body of liquid retained in the upper flask.

OPERATION

Nine hundred milliliters of the solvent composition (1,1,1-trichloroethane plus the enumerated inhibitor) under study was placed into the bottom flask. The entire apparatus was covered with aluminum foil to exclude light and to retain some warmth in the overhead flask, such as occurs in the warm dip of a degreaser. Heat was applied to the lower flask and a moderate reflux rate maintained for 24 hours.

At the end of this period, the apparatus was allowed to cool and the two solvent portions analyzed for stabilizer concentrations and aliquots subjected to the "Waring Blendor Test."

In this manner, there is obtained the data to calculate a factor representing the proportion of the inhibitor which will go overhead with the vapors and that proportion which will remain behind in the sump liquid in a conventional vapor degreaser. The factors determined by this experiment are referred to as partitioning factors for the top and bottom. The partitioning factors were determined by analyzing the top fraction and the bottom fraction of the partitioning experiment for each inhibitor, determining the percent inhibitor in each of the top and bottom fractions and normalizing these values to a decimal value on the basis of that fraction of solvent to a unit (100% basis). Thus, for dioxolane, it was determined that ca. 55 weight percent of the inhibitor in the original composition was found in the top fraction of the partitioning experiment (50% by volume of the original amount) and ca. 45 weight percent was found in the bottom fraction. Normalizing these values:

$$\text{Top Partitioning Factor} = \frac{0.55}{.5} = 1.1$$

-continued $$\text{Bottom Partitioning Factor} = \frac{0.45}{.5} = 0.9$$

The partitioning factors for each inhibitor were run several times and the average of the values obtained from these several runs was calculated. The values for each inhibitor under consideration are set forth below:

in percent of inhibitor found. The minimum concentration for protection in top and bottom is found by dividing the value determined as the concentration for APHA color < 1000 by the smallest partitioning factor for the inhibitor.

Thus, for dioxolane:

$$\text{Minimum concentration for dioxolane} = \frac{< 1000 \text{ APHA conc.}}{\text{Partition Fraction}} = \frac{4.0}{.9} = 4.4$$

The final concentration in each of the top and bottom of a system employing the minimum concentration is found in the last column.

| Inhibitor | Conc. for APHA of <1000 after Waring Blendor Test | Partition Factor Top | Partition Factor Bottom | Minimum Conc.* for Protection Top and Bottom Wt. % | Starting with Min. Conc. (previous col.) Final Conc. Top Wt. % | Starting with Min. Conc. (previous col.) Final Conc. Bottom Wt. % |
|---|---|---|---|---|---|---|
| Dioxolane | 4.0 wt. % | 1.06 | 0.9 | 4.4 | 5.2 | 4.0 |
| t-Butyl Alcohol | 4.2 | 1.42 | 0.51 | 8.2 | 11.6 | 4.2 |
| Nitromethane | 3.1 | 1.28 | 0.72 | 4.4 | 5.7 | 3.1 |
| Trioxane | 2.6 | 0.52 | 1.47 | 5.0 | 2.6 | 7.3 |
| Butylene Oxide | 9.8 | 1.20 | 0.80 | 12.2 | 14.6 | 9.8 |
| Dioxane | 1.6 | 0.47 | 1.52 | 3.4 | 1.6 | 5.2 |

*(Initial Conc.) / (Part. Factor) = Conc. for APHA of <1000, e.g., for dioxolane:
$\frac{4.0}{.9} = 4.4$ wt. %

| | Partition Factor Top | Partition Factor Bottom | Partition Factor as Percent in: Top | Partition Factor as Percent in: Bottom |
|---|---|---|---|---|
| Dioxane | 0.47 | 1.52 | 23.6 | 76.4 |
| Trioxane | 0.52 | 1.47 | 26.2 | 73.8 |
| Dioxolane | 1.06 | 0.9 | 54 | 45 |
| NM¹ | 1.28 | 0.72 | 64.7 | 35.3 |
| BO¹ | 1.2 | 0.8 | 60 | 40 |
| TBA¹ | 1.42 | 0.51 | 73.5 | 26.5 |

¹NM = Nitromethane; BO = Butylene Oxide; and TBA = Tertiary Butyl Alcohol

The Waring Blendor Test comprises placing 100 ml. of the composition being tested, at room temperature, in a Waring Blendor with 10 grams of 1100 aluminum chips and running the blender for 10 minutes, then filtering the sample and determining the APHA color of the filtrate.

The Waring Blendor Test is the most severe test developed and correlates with conditions found in the sump and still when many fines are present and the heating source is operated near its maximum because of poor heat transfer caused by encrustation of heat transfer surfaces and/or excessive metal fines or chips content, and accumulation of high boiling oily contaminants coupled with local hot spots resulting from localized spots of no encrustation.

The results of such testing established the minimum concentration of each inhibitor which was required to be present in an original composition to enable the condensate of the vapors as well as the sump to be essentially nonreactive to aluminum. The following table gives the results obtained employing only the named inhibitor and 1,1,1-trichloroethane.

The concentration for APHA color of < 1000 is chosen as the criterion for substantially no reaction after the Waring Blendor Test. The analysis for inhibition in the top fraction and bottom fraction is set forth This conc. will give good protection in top and bottoms fractions.

To demonstrate the effect of two-component systems in the sump of a refluxing system with and without small amounts of butylene oxide and nitromethane on zinc at 3.5 wt. percent dioxane and tertiary butyl alcohol, the following data is submitted compared with a three-component system in which trioxane is present:

| 3.5 wt. % | | | | |
|---|---|---|---|---|
| Dioxane | Dioxolane | TBA | .5 Wt. % each CH₃NO₂ and butylene oxide | Zinc as zinc chloride ppm |
| (70%) 2.45 | 0 | (30%) 1.05 | 0 | 6300 |
| (70%) 2.45 | 0 | (30%) 1.05 | — | 4 |
| (50%) 1.75 | 0 | (50%) 1.75 | 0 | 5400 |
| (50%) 1.75 | 0 | (50%) 1.75 | — | 5 |
| (20%) 0.7 | 0 | (80%) 2.8 | 0 | 4400 |
| " | 0 | " | — | 16 |

Compared with a three-component system consisting of dioxane, trioxane and tert. butyl alcohol with and without nitromethane and butylene oxide:

| Dioxane | Trioxane | TBA | 0.5% wt. each of CH₃NO₂ and butylene oxide | Zinc as zinc chloride ppm |
|---|---|---|---|---|
| (40%) 1.4 | (20%) .7 | (40%) 1.4 | 0 | 300 |
| (40%) 1.4 | (20%) .7 | (40%) 1.4 | — | 5 |
| (25%) 0.875 | (25%) 0.875 | (50%) 1.75 | 0 | 200 |
| " | " | " | — | 7 |
| (33%) | (33%) | (33%) | 0 | 100 |

-continued

| dioxane | dioxolane | TBA | 0.5% wt. each of CH₃NO₂ and butylene oxide | Zinc as zinc chloride ppm |
|---|---|---|---|---|
| 1.165 " (60%) | 1.165 " (20%) | 1.165 " (20%) | — | 4 |
| 2.1 " (20%) | .7 " (60%) | .7 " (20%) | 0 | 1200 |
| .7 " | 2.1 " | .7 " | — | 3 |
| | | | 0 | 1 |
| | | | — | 100 |

Figure 8:
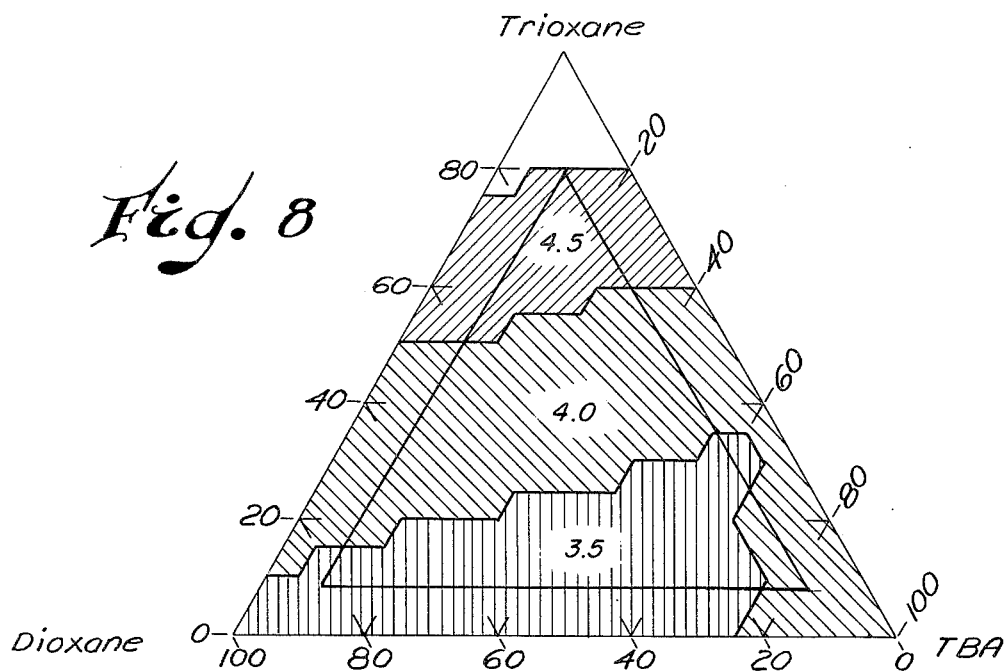
Figure 9:
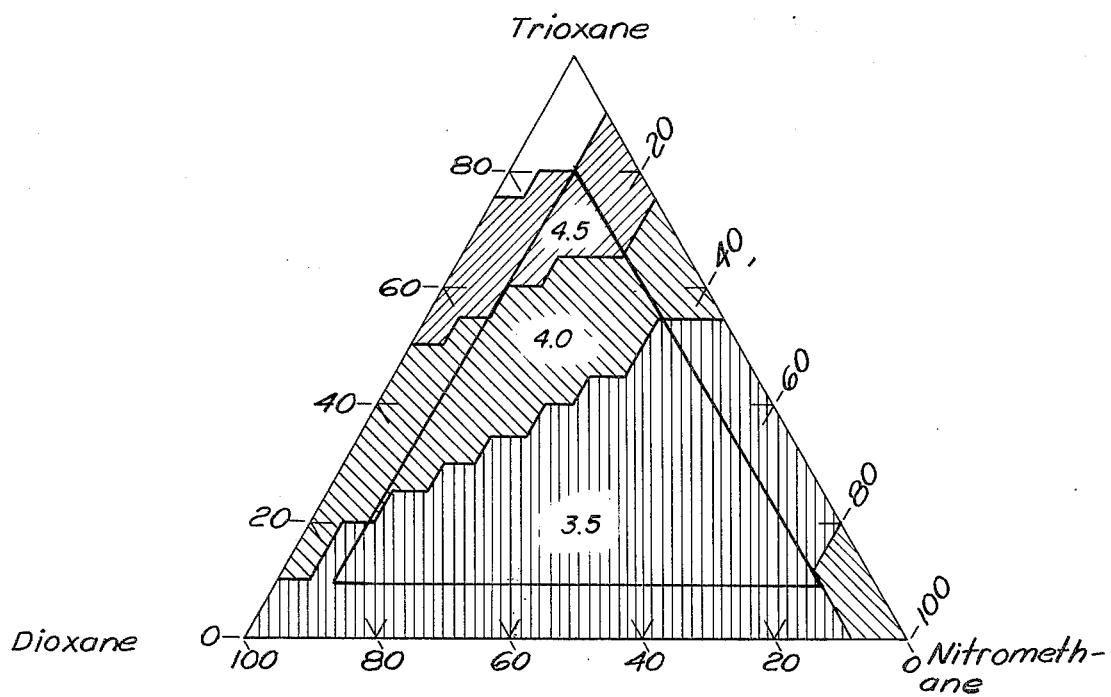

Thus, the data of the last three compositions of the table demonstrates that while 3.5 weight percent of the three-component system with nitromethane and butylene oxide is satisfactory with regard to zinc, the 3.5 weight percent of the same composition is insufficient to prevent attack on aluminum in the vapor as shown in FIG. 8. Wherein it is shown that there is required 4 or 4.5 weight percent to protect against aluminum top and bottom. This is because trioxane is less agressive to zinc (thus less zinc chloride when it is present) yet is not as good an aluminum stabilizer (thus more trioxane, a bottom factor, must be present than can be obtained in a 3.5% wt. total three-component system to provide sufficient inhibitor to the top).

What is claimed is:

1. A 1,1,1-trichloroethane composition stable in the liquid and vapor phases in the presence of aluminum, zinc, copper, iron and their alloys which consists of 1,1,1-trichloroethane and based on the total weight of the composition (A) 3.5 to 4.5 weight percent of a mixture selected from the following:
  a. dioxane, dioxolane and trioxane;
  b. dioxane, dioxolane and nitromethane;
  c. dioxane, trioxane and nitromethane;
  d. dioxane, dioxolane and tert. butyl alcohol;
  e. dioxane, trioxane and tert. butyl alcohol;
  f. dioxolane, trioxane and nitromethane;
  g. dioxolane, trioxane and tert. butyl alcohol;
  h. dioxane, tert. butyl alcohol and nitromethane; and
  i. trioxane, tert. butyl alcohol and nitromethane,
and (b) as the essential acid acceptor from about 0.25 to about 1 percent by weight of a $C_{3-8}$ monoalkylene epoxide, epichlorohydrin or cyclohexene epoxide, provided that when nitromethane is not a compound selected from the list above at least 0.25 to about 0.8 weight percent nitromethane is present, said compositions (a) through (i) being within the parameters of the inner triangle of the appropriate FIGS. 1–9.

2. The composition of claim 1 wherein the said three components are dioxane, dioxolane and trioxane.

3. The composition of claim 1 wherein the said three components are dioxane, dioxolane and nitromethane.

4. The composition of claim 1 wherein the said three components are dioxane, trioxane and nitromethane.

5. The composition of claim 1 wherein the said three components are dioxane, dioxolane and tert. butyl alcohol.

6. The composition of claim 1 wherein the said three components are dioxane, trioxane and tert. butyl alcohol.

7. The composition of claim 1 wherein the said three components are dioxolane, trioxane and nitromethane.

8. The composition of claim 1 wherein the said three components are dioxolane, trioxane and tert. butyl alcohol.

9. The composition of claim 1 wherein the said three components are dioxane, tert. butyl alcohol and nitromethane.

10. The composition of claim 1 wherein the said three components are trioxane, tert. butyl alcohol and nitromethane.

11. The composition of claim 1 wherein the said three components are trioxane, tert. butyl alcohol and nitromethane.

* * * * *

UNITED STATES PATENT AND TRADEMARK OFFICE
CERTIFICATE OF CORRECTION

PATENT NO. : 4,018,837
DATED : April 19, 1977
INVENTOR(S) : Wesley L. Archer et al.

It is certified that error appears in the above-identified patent and that said Letters Patent are hereby corrected as shown below:

In [75] the inventor "Raymond R. Gerard" should be -- Raymond T. Gerard --.

Col. 1, line 8, "Aug. 16." should be -- Aug. 16, --.

Col. 2, line 6, "Shorly" should read -- Shortly --.

Cols. 3 and 4, the second patent number "2,933,747" should be -- 2,923,747 --.

The following changes should also be made in Cols. 3 and 4:

Under the heading 3,000,978:
  line 21, across from "Secondary alcohols" delete "X";
  line 22, across from "Tertiary alcohols" insert -- X --.

Under the heading 3,070,634:
  line 19, across from "Butylene oxide/oxiranes" delete "X";
  line 20, across from "Acetylenic alcohols" delete " /X* " and insert -- X --;
  line 21, across from "Secondary alcohols" delete " /X " and insert -- /X* --;
  line 23, across from "Primary alcohols" insert -- /X --.

Under the heading 3,099,694:
  line 16, across from "Trioxane" delete "X";
  line 17, across from "Dioxolane" insert -- X --;
  line 18, across from "Dioxane" delete "X";
  line 19, across from "Butylene oxide/oxiranes" insert -- X --

UNITED STATES PATENT AND TRADEMARK OFFICE
CERTIFICATE OF CORRECTION

PATENT NO. : 4,018,837

DATED : April 19, 1977

INVENTOR(S) : Wesley L. Archer et al.

It is certified that error appears in the above-identified patent and that said Letters Patent are hereby corrected as shown below:

Under the heading 3,113,156:

line 12, across from "Perchloroethylene" delete "X";
line 13, across from "Nitroalkanes (nitromethane)" insert -- X --;
line 16, across from "Trioxane" delete "X";
line 17, across from "Dioxolane" insert -- X --.
(see attached photocopy)

Col. 9, lines 43, 49 and 67 place quotation marks around -- "Waring Blendor Test" --.

Col. 10, lines 29 and 30, delete "bottoms" and insert -- bottom --.

Signed and Sealed this

Thirtieth Day of May 1978

[SEAL]

Attest:

RUTH C. MASON
Attesting Officer

LUTRELLE F. PARKER
Acting Commissioner of Patents and Trademarks